United States Patent [19]
White

[11] Patent Number: 4,593,689
[45] Date of Patent: Jun. 10, 1986

[54] ENDOTRACHEAL TUBE INCLUDING MEANS FOR PATIENT COMMUNICATION

[76] Inventor: Kenneth S. White, 4910 Richardson Dr., Wilmington, N.C. 28405

[21] Appl. No.: 723,368

[22] Filed: Apr. 15, 1985

[51] Int. Cl.⁴ .............................................. A61M 16/00
[52] U.S. Cl. ........................... 128/201.19; 128/207.15; 128/207.18
[58] Field of Search ...................... 128/201.19, 207.14, 128/207.15, 207.16, 207.18

[56] References Cited

U.S. PATENT DOCUMENTS

| | | | |
|---|---|---|---|
| 3,972,321 | 8/1976 | Proctor | 128/207.18 |
| 4,037,605 | 7/1977 | Firth | 128/207.15 |
| 4,150,676 | 4/1979 | Jackson | 128/207.15 |
| 4,280,492 | 7/1981 | Latham | 128/207.15 |
| 4,435,853 | 3/1984 | Blom et al. | 3/1.3 |
| 4,449,523 | 5/1984 | Szachowicz et al. | 128/207.15 |
| 4,459,984 | 7/1984 | Liegner | 128/207.15 |

FOREIGN PATENT DOCUMENTS 2096467  10/1982  United Kingdom .......... 128/207.15

*Primary Examiner*—Henry J. Recla
*Attorney, Agent, or Firm*—Willian Brinks Olds Hofer Gilson & Lione

[57] ABSTRACT

An endotracheal tube for allowing nasally intubated patients to speak comprising an elongated tube adapted for nasal intubation. The tube has an opening adjacent the patient's throat when intubated, and reed means in the opening. Interconnected first and second valves are at the proximal tube end and the opening, respectively, and are manually operable to open the tube proximal end and close the opening, and vice versa. The patient can breathe through the tube when the tube proximal end is open and the opening is closed. When the tube proximal end is closed and the opening is open, expiring air from the patient's lungs passes the reed means causing it to vibrate and produce an audible tone which can be altered by the patient's mouth and tongue to produce audible speech.

7 Claims, 7 Drawing Figures

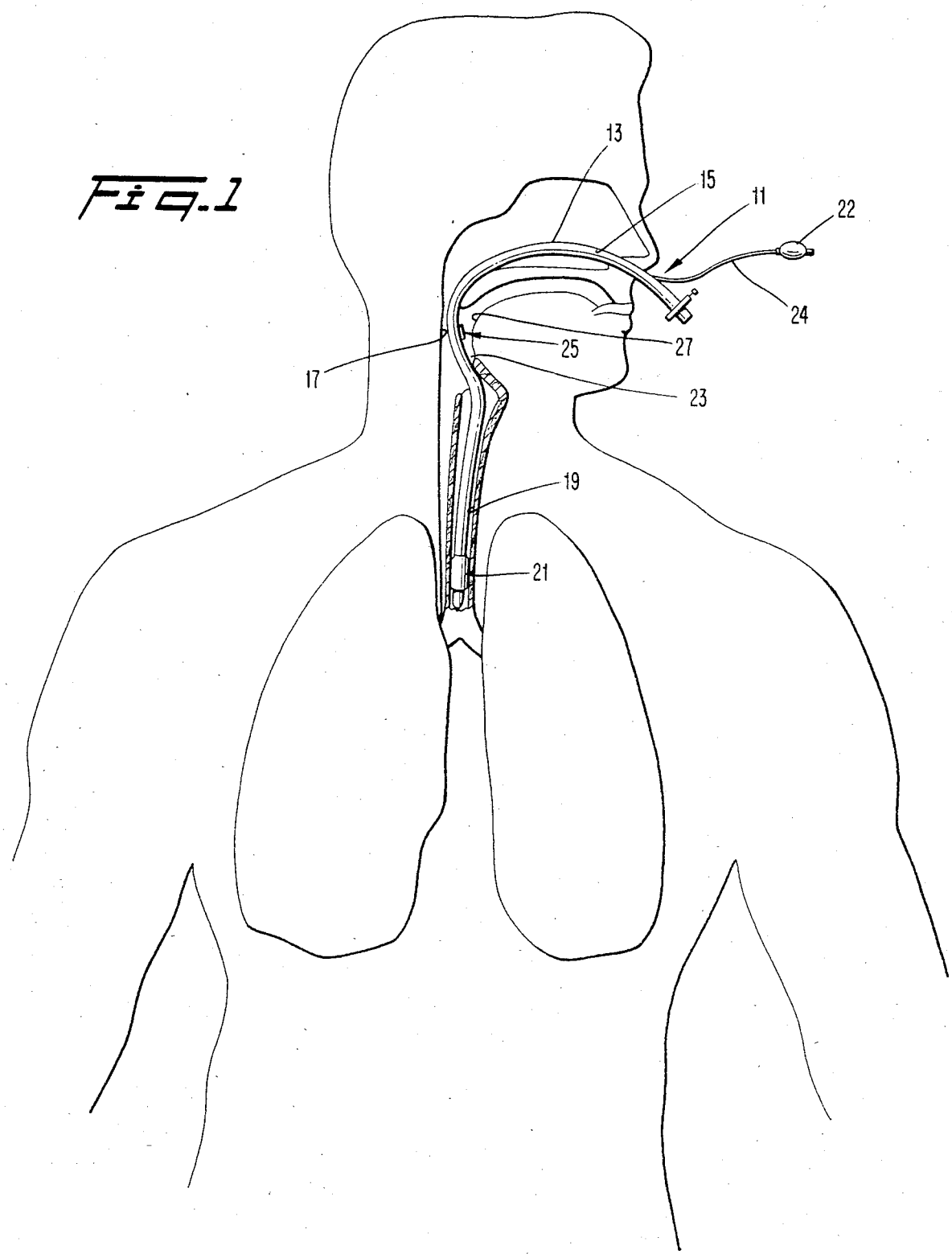

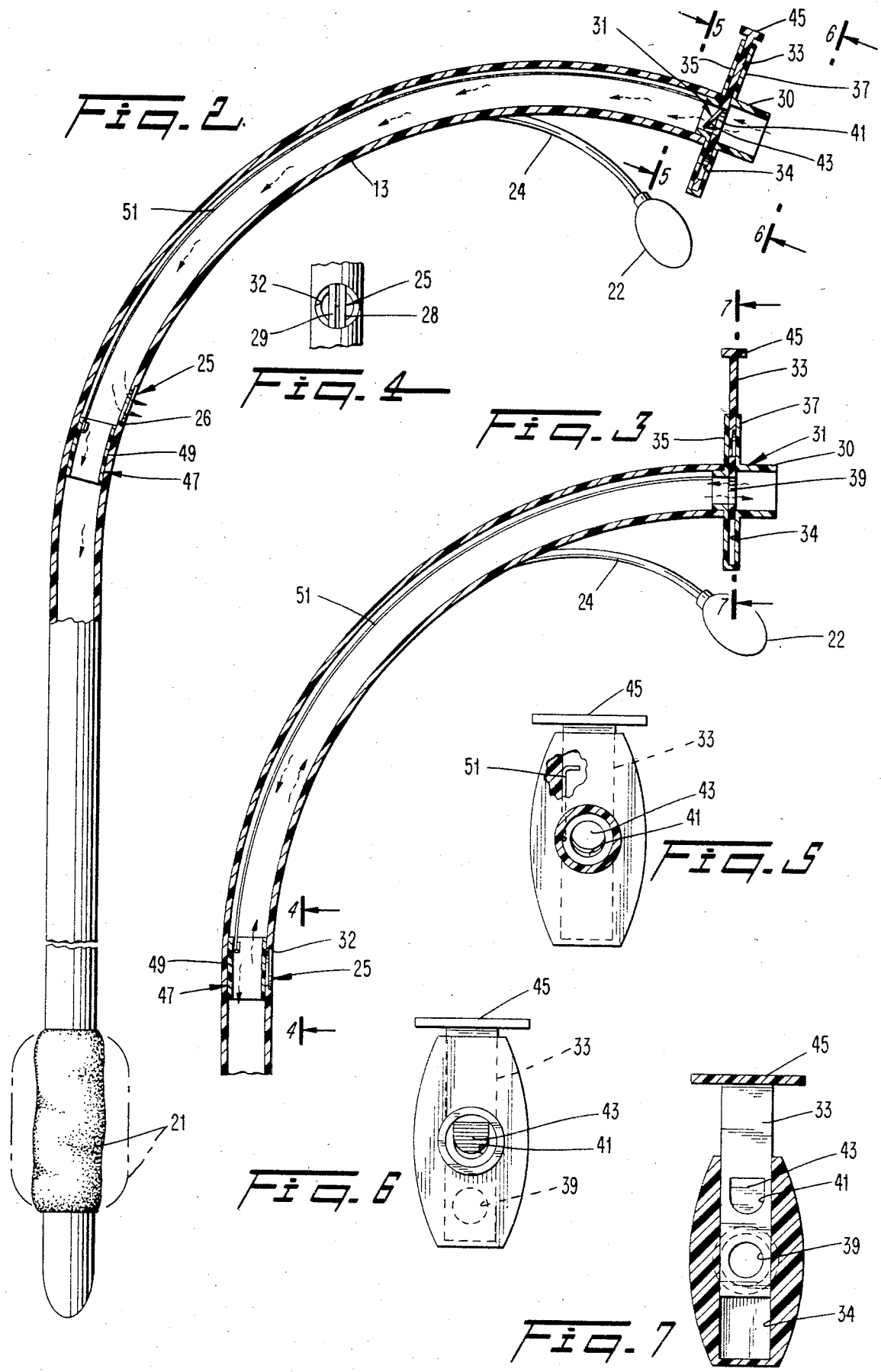

ENDOTRACHEAL TUBE INCLUDING MEANS FOR PATIENT COMMUNICATION

BACKGROUND OF THE INVENTION

This invention relates generally to endotracheal tubes, and more particularly to one which is operable to allow a patient to verbally communicate while nasally intubated.

Endotracheal tubes are placed within the trachea of a patient to assist in breathing. Those which are to remain in place for a relatively long period of time often are intubated or inserted nasally, so that the tube extends through the nasal passage, past the vocal chords, and into the trachea. While in place, substantially all of the air inhaled and expired by the patient passes through the endotracheal tube. Thus, no air passes by the vocal chords of the patient so that while intubated, the patient cannot speak. Not being able to speak poses severe physical and psychological problems to the patient. Thus, there is a strong need for an endotracheal tube which would allow a nasally-intubated patient to speak.

SUMMARY OF THE INVENTION

The present invention is directed to an endotracheal tube which is selectively operable to permit expired air to pass through the mouth of the intubated patient. The tube includes a device which is operable by this expired air to produce an audible tone which can be altered by the patient's lips and tongue to produce audible words.

The endotracheal tube includes a valve construction which is selectively manually operable to cause air which is expired from the patient's lungs to flow either through the tube and to exit the proximal end of the tube, or to flow through the patient's mouth. Means, preferably a reed device, is positioned in the tube and is actuated by expired air passing into the patient's mouth to produce an audible sound or tone. This tone can be altered by the patient's lips and tongue to produce intelligible speech.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out the appended claims.

To achieve the objects and in accordance with the purpose of the invention, as embodied and broadly described herein, the endotracheal tube of this invention comprises an elongated tube adapted for nasal intubation, the tube having means positioned adjacent a patient's throat during intubation and operable to produce an audible tone in voice range when expired air is passed by it, means for selectively blocking and allowing passage of expired air from the patient past the tone producing means, the audible tone produced being alterable by the patient's lips and tongue to produce intelligible speech.

Broadly, the tone producing means includes a reed means, and the tube has a proximal end, a manually-operable first valve at the proximal end operable to selectively open and close the tube, and a second valve adjacent the reed means. Preferably, the first valve is operable to open when the second valve blocks passage of air past the reed means, and to close when the second valve allows passage of expired air past the reed means and during expiration. The first valve is constructed so that when operated to its closed position, it allows the patient to inhale. The first and second valves can be interconnected for conjoint operation. Preferably, the reed means is disposed in an opening in the tube which is positioned at the throat area when the tube is intubated, and the second valve is operable to cover and uncover the opening.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1 is a schematic view illustrating an endotracheal tube constructed in accordance with the invention and nasally intubated in a patient;

FIG. 2 is an enlarged view, partly in section, of the endotracheal tube of this invention showing the parts in position for patient communication;

FIG. 3 is a view similar to FIG. 2 showing the parts in position for breathing and non-communication;

FIG. 4 is a plan view of a portion of FIG. 3 taken along the line 4—4 and looking in the direction of the arrows;

FIG. 5 is an enlarged sectional view of FIG. 2 taken along the line 5—5 thereof;

FIG. 6 is an enlarged end view of FIG. 2 taken along the line 6—6 and looking in the direction of the arrows; and FIG. 7 is an enlarged sectional view of FIG. 3 taken along the line 7—7 thereof.

DESCRIPTION OF THE PREFERRED EMBODIMENT

Reference will now be made in detail to the present preferred embodiment of the invention, an example of which is illustrated in the accompanying drawings.

The preferred embodiment of endotracheal tube is shown in FIG. 1 and is represented generally by the numeral 11. The endotracheal tube comprises an elongated tube adapted for nasal intubation. As embodied herein, an elongated tube 13 is shown in FIG. 1 as extending into and through a nasal passage 15 of a patient, and downwardly through a pharynx 17, and into a windpipe 19. The tube is provided with an inflatable cuff 21 toward its distal end which is inflated after insertion so that inhaled and expired air is caused to flow through the tube 13. A cuff inflator 22 is connected by a tube 24 to the cuff 21 for inflating the latter as will be understood by those skilled in the art.

It will also be understood that a nasally-intubated patient normally is unable to speak. This is so because all of the expired air is caused to pass through the tube 13 and therefore is unavailable to actuate the patient's vocal chords which are located in the area of the larynx illustrated by the numeral 23. This poses physical problems for many patients and often causes psychological trauma. Thus, it is very desirable that such nasally intubated patients be provided with some means whereby they can vocally communicate with others.

In accordance with the invention, the tube has means positioned adjacent a patient's throat during intubation which is operable to produce an audible tone in voice range when expired air is passed it. As embodied herein, reed means 25 is provided in the wall of the tube 13. As shown in FIG. 1, the reed means 25 is located adjacent the patient's throat 27 when the tube 13 is nasally intubated and includes a pair of spaced reeds 29, 31 which are disposed across the opening 33 in the tube 13. The reeds 29, 31 are constructed so that when expired air passing through the tube 13 is permitted to pass through the opening 33, the reeds 29, 31 are caused to vibrate and to produce an audible tone in voice range.

Any one of a number of suitable reed constructions may be used although it is contemplated that reed sheets or strands mounted as shown and constructed of suitable plastic or silicon rubber and spaced apart a distance so that expired air causes the reeds to vibrate from about 100 to about 200 cps will be acceptable, although frequencies outside the range may be used.

In accordance with the invention, means is provided for selectively blocking and allowing passage of expired air from the patient past the tone producing means. As embodied herein, the tube 13 has a proximal end 30, and a manually operable first valve 31 is provided at the proximal end to selectively open and close the tube 13. The first valve 31 includes a slide 33 slidably guided in a slot 34 in the tube 13 and between spaced apart flanges 35, 37 integral with or suitably fixed to the tube 13. The slide 33 has a pair of spaced openings 39, 41 formed therein. A flapper valve 43 is connected to the slide 33 and is operable to open or close the opening 41 as will be disclosed below. The slide 33 has a "T" 45 formed integral therewith for manual operation of the side 33.

The slide is manually movable from a first position shown in FIG. 2, to a second position, shown in FIG. 3. In the first position shown in FIG. 2, the opening 41 is aligned with the tube 13 so that when the tube 13 is intubated, the patient may inhale air through the tube 13 past the flapper valve 43. With the slide 33 in this first position, the flapper valve 43 closes when the patient exhales and blocks the opening 41 and the tube 13.

When the slide 33 is in the second position shown in FIG. 3, the opening 39 in slide 33 is aligned with the tube 13 so that free passage (both inhaling and exhaling) is permitted through tube 13.

In accordance with the invention, a second valve is adjacent the tone producing means and is operable to selectively block and permit passage of expired air from the patient past the tone producing means. The first valve is operable to open when the second valve blocks passage of air past the tone producing means, and to close when the second valve allows passage of expired air past the tone producing means.

As embodied herein, a second valve 47 is constructed of a hollow cylindrical member 49 and is slidably disposed in the tube 13 adjacent the opening 33. The valve cylinder 49 is movable from a first position, shown in FIG. 2, where it is spaced from the opening 33, to a second position, shown in FIG. 3, when it overlaps and closes the opening 33. In the position shown in FIG. 2, expiring air from the patient's lungs closes the flapper valve 43 and is caused to exit the tube 13 through opening 33. In the FIG. 3 position, expiring air (and inhaled air, passes through the tube 13 only, exiting and entering through proximal end 30.

As further embodied herein, a connecting wire, such as a Bowden wire 51, interconnects the slide 33 and the cylinder 49 so that when the slide 33 is moved to the first position, shown in FIG. 2, the cylinder 49 is also moved to the position shown in that figure. Similarly, when the slide 33 is moved to its second position, shown in FIG. 3, the cylinder 49 also moves to the position shown in that figure. Suitable guide means (not shown) is provided for the Bowden wire 51 as will be understood by those skilled in the art.

In accordance with the invention, the audible tone produced by the tone producing means is alterable by the patient's lips and tongue to produce intelligible speech. As embodied herein, it will be appreciated that expiring air passing the reeds 29, 31 when the first and second valves 31, 47 are in the position shown in FIG. 2 produces a tone much in the nature of the tone produced by a patient's own vocal chords. The tone produced by the vibrating reeds 29, 31 is a monotone. Nevertheless, the patient is capable of altering that tone by his tongue and lips in much the same manner as he normally speaks. Thus, the tone produced by the reeds 29, 31 allows the patient to speak.

In use of the endotracheal tube 11, the valve 31 is normally open and the valve 47 is normally closed, as shown in FIG. 3. This allows the patient to freely inhale and exhale with all air passing through the tube 13 and its proximal end 30 which is the normal procedure for endotracheal tubes. When the patient desires to speak, he need only move the slide 33 to the position shown in FIG. 2. In this position of the slide 33, flapper valve 43 opens when the patient inhales, but closes when he exhales. At the same time, the valve 47 is open so that expired air passes through the opening 32 and past the reeds 29, 31 causing them to vibrate and produce the audible tone. The patient, by manipulating his tongue and lips as in normal speaking is able to alter this tone to produce intelligible speech, i.e., audible words. When the patient is finished speaking, he can move the slide 33 to reopen the valve 39 and close the valve 47.

The slide 33 is illustrated as movable manually from the first to the second position illustrated in FIGS. 2 and 3. It will be appreciated that the slide 33 can be movably biased toward the position shown in FIG. 3 by suitable spring means (not shown) and manually movable toward the FIG. 2 position against the biasing force so that upon releasing the slide 33, the parts move back to the FIG. 3 position.

Also, the depicted structure includes a flapper valve 43 on the slide 33 to allow the patient to inhale when the slide 33 is in the FIG. 2 position and the valve 47 is open for "speaking." It will be understood that other one-way or equivalent valve structures can be substituted for the illustrated flapper valve 43.

By this invention, there has been provided a novel endotracheal tube construction which includes means for allowing a patient to speak during nasal intubation, which is calculated to fulfill the inventive objects hereinabove set forth. While a preferred embodiment has been set forth and described in detail herein, it will be apparent to those skilled in the art that various additions, substitutions, modifications and omissions can be made to the endotracheal tube of the present invention without departing from the scope or spirit of the invention. Thus, it is intended that the present invention cover the additions, substitutions, modifications and omissions provided they come within the scope of the appended claims and their equivalents.

What is claimed is:

1. An endotracheal tube for allowing nasally-intubated patients to speak, comprising an elongated tube adapted for nasal intubation, said tube having means positioned adjacent a patient's throat during intubation and being operable to produce an audible tone in voice range when expired air is passed by it, means for selectively blocking and allowing passage of expired air past said tone producing means, said audible tone being alterable by the patient's lips and tongue to produce intelligible speech.

2. The endotracheal tube claimed in claim 1, said tone producing means comprising reed means operable to vibrate when expired air is passed by it to produce a tone in the audible voice range.

3. The endotracheal tube claimed in claim 2, said reed means being disposed adjacent an opening in said tube, said selective blocking means including a valve selectively movable to block and unblock said opening.

4. The endotracheal tube claimed in claim 2, said reed means including at least a pair of reeds constructed and spaced to vibrate at a frequency of from about 100 to about 200 cps under the influence of expiring air.

5. The endotracheal tube claimed in claim 1, said tube having a proximal end, a manually-operable first valve at said proximal end operable to selectively open and close said tube, a second valve adjacent said tone producing means, said first and second valves being interconnected so that said first valve opens when said second valve closes, and vice versa.

6. The endotracheal tube claimed in claim 5, said first valve including one-way valve means operable, when said first valve is closed, to permit passage of air from outside said tube to said patient when said patient inhales, and to prevent said patient from exhaling past said first valve.

7. The endotracheal tube claimed in claim 5, said first and second valves being interconnected by an elongated wire passing through said tube.

* * * * *

UNITED STATES PATENT AND TRADEMARK OFFICE
CERTIFICATE OF CORRECTION

PATENT NO. : 4,593,689

DATED : June 10, 1986

INVENTOR(S) : Kenneth S. White

It is certified that error appears in the above-identified patent and that said Letters Patent is hereby corrected as shown below:

```
In Column 3, line 2,  "31" should be "28"
In Column 3, line 3,  "33" should be "32"
In Column 3, line 4,  "31" should be "28"
In Column 3, line 6,  "33" should be "32"
In Column 3, line 6,  "31" should be "28"
In Column 3, line 28, "side" should be "slide"
In Column 3, line 51, "33" should be "32"
In Column 3, line 53, "33" should be "32"
In Column 3, line 55, "33" should be "32"
In Column 3, line 58, "33" should be "32"
In Column 4, line 7,  "31" should be "28"
In Column 4, line 11, "31" should be "28"
In Column 4, line 15, "31" should be "28"
In Column 4, line 27, "31" should be "28"
```

Signed and Sealed this

Seventh Day of October, 1986

[SEAL]

*Attest:*

DONALD J. QUIGG

*Attesting Officer*  *Commissioner of Patents and Trademarks*